United States Patent
Liu et al.

(10) Patent No.: US 11,860,171 B1
(45) Date of Patent: Jan. 2, 2024

(54) SCREENING KIT AND DIAGNOSIS SYSTEM FOR PRIMARY ALDOSTERONISM

(71) Applicant: Hangzhou Calibra Diagnostics Co., Ltd., Hangzhou (CN)

(72) Inventors: Pengyun Liu, Hangzhou (CN); Xiaofen Yuan, Hangzhou (CN); Jinfei Ma, Hangzhou (CN); Ziqing Kong, Hangzhou (CN); Yikun Li, Hangzhou (CN); Weijia Wu, Hangzhou (CN); Huafen Liu, Hangzhou (CN)

(73) Assignee: HANGZHOU CALIBRA DIAGNOSTICS CO., LTD., Hangzhou (CN)

( * ) Notice: Subject to any disclaimer, the term of this patent is extended or adjusted under 35 U.S.C. 154(b) by 0 days.

(21) Appl. No.: 18/304,915

(22) Filed: Apr. 21, 2023

(30) Foreign Application Priority Data

Jul. 13, 2022 (CN) .......................... 202210819638.2

(51) Int. Cl.
*G01N 33/74* (2006.01)
*G01N 1/34* (2006.01)
*G01N 33/68* (2006.01)

(52) U.S. Cl.
CPC ............. *G01N 33/743* (2013.01); *G01N 1/34* (2013.01); *G01N 33/6848* (2013.01)

(58) Field of Classification Search
None
See application file for complete search history.

(56) References Cited

U.S. PATENT DOCUMENTS

| 8,426,214 B2 * | 4/2013 | Stayton ............ G01N 33/54333 |
| | | 435/173.9 |
| 2017/0138940 A1 | 5/2017 | Goethel et al. |
| 2020/0124622 A1 | 4/2020 | Satoh et al. |

FOREIGN PATENT DOCUMENTS

| CN | 112014509 A | 12/2020 |
| CN | 114354806 A | 4/2022 |
| CN | 114487210 A | 5/2022 |
| CN | 114544836 A | 5/2022 |
| WO | WO-2020045497 A1 | 3/2020 |

* cited by examiner

*Primary Examiner* — Xiaoyun R Xu
(74) *Attorney, Agent, or Firm* — MUNCY, GEISSLER, OLDS & LOWE, P.C.

(57) ABSTRACT

In a screening kit and a confirmed and typing diagnosis system for primary aldosteronism, a sample is pretreated by a magnetic bead bonded with a balanced hydrophilic-lipophilic polymer on the surface thereof, and process conditions are optimized and the content of each the five markers such as, aldosterone in the sample is accurately detected by liquid chromatography-tandem mass spectrometry for one time, thus finding the optimal screening cut-off value of 20.4; when a positive result is judged, PA is confirmed and subjected to typing diagnosis according to the test values of the markers, thereby achieving the simultaneous detection of the content of each the five markers such as, aldosterone on the same platform. Therefore, the screening kit and confirmed and typing diagnosis system for primary aldosteronism are integrated with screening, confirmed and typing diagnosis functions, thus providing a reliable laboratory examination basis for clinicians to formulate an effective therapeutic regimen.

2 Claims, 6 Drawing Sheets

SCREENING KIT AND DIAGNOSIS SYSTEM FOR PRIMARY ALDOSTERONISM

CROSS-REFERENCE TO RELATED APPLICATIONS

The present application claims priority to a Chinese prior application No. CN202210819638.2 and filed on Jul. 13, 2022; the entire contents of the above application, including the description, claims, abstract and abstract drawings of which are incorporated herein as a portion of the present invention.

TECHNICAL FIELD

The present invention relates to the field of medical diagnosis, and in particular to a screening kit, and a confirmed and typing diagnosis system for primary aldosteronism.

BACKGROUND OF THE INVENTION

Primary Aldosteronism (PA) refers that excessive aldosterone is spontaneously secreted by adrenal gland to cause sodium retention and potassium discharge in vivo as well as increased blood volume, and the activity of the renin-angiotensin system is inhibited. PA is clinically manifested as hypertension accompanied with or without hypokalemia. The latest domestic study has shown that the incidence of PA exceeds 4% in the newly diagnosed hypertension and 17-23% in the refractory hypertension group. Compared with the essential hypertension patients, PA patients have a higher risk of suffering from atherosclerosis, myocardial infarction, peripheral vascular diseases, stroke and chronic renal damage, and it is easy to cause missed diagnosis and misdiagnosis. Therefore, early diagnosis and early treatment are of great importance. The most common two forms of PA are aldosterone-producing adenoma (APA) and bilateral idiopathic hyperaldosteronism (IHA); APA can be cured by adrenal gland surgery to improve arterial hypertension; and for the patients who refuse or are not suitable for surgery, drug intervention is an effective choice.

PA diagnosis includes screening, confirmed and typing diagnosis. Aldosterone/renin activity (ARR) is the preferred screening indicator for PA. Positive patients screened can be confirmed by oral administration of diet high-sodium, fludrocortisone test (FST), saline solution test (SIT) or captopril test (CCT), and unilateral dominant or bilateral equilibrium PA is distinguished by adrenal CT, adrenal venous sampling (AVS) and other ways. There are the following aspects of reasons to interfere the confirmed diagnosis of PA:

1) Test Method

Test for aldosterone/renin activity (ARR) is the common PA biochemical test index at present, but different test methods will affect the accuracy of the ARR test value, especially, the quantitative result of aldosterone; the test is throughout the whole process of screening, diagnosis and typing diagnosis. Currently, the measurement of aldosterone mainly includes radioimmunoassay and chemiluminescent immunoassay. Even though the method is rapid and easy to be implemented, the method has the disadvantages of cross-reactivity and poor interlaboratory test comparability. Besides no comparability and lack of standardization in the test method, in case of renal function damage, the use of immunoassay will cause significantly overestimated test result of aldosterone; IA indicates that the median positive bias is 127%; it is presumably caused by the cross reaction between antibodies and non-eliminated aldosterone metabolites. Such an action is not only limited to end-stage renal failure, but also occurs in patients with mild or moderate renal insufficiency in a grading way. Therefore, there is frequently a phenomenon of inconsistency between the test result and clinical manifestation, which affects the screening and differential diagnosis for the pathogenesis of secondary hypertension by a clinician, and even leads to misdiagnosis or missed diagnosis of PA patients.

2) Interference from Therapeutic Drugs

Recommended by domestic and overseas guidelines, test for aldosterone/renin activity is the preferred biochemical index to screen primary aldosteronism. However, the renin-angiotensin-aldosterone system of a human body is highly susceptible to diet and drugs; therefore, patients need to withdraw the conventional hypotensive drugs (such as, calcium ion antagonists, angiotoninase inhibitors, angiotensin II receptor antagonists and diuretics) for 4-6 weeks during screening, which causes a false-positive or false-negative screening result and causes certain difficulties to the clinical implementation of screening items. This is solved by the applicant in the patent invention 2021106374412 of the prior application, namely, how to eliminate the false-positive or false-negative drug interference.

3) Differential Diagnosis

In the differential diagnosis of endocrine hypertension, there is always hypertension caused by other excessive mineralocorticoids. There exist clinical symptoms similar to primary aldosteronism, which causes certain disturbances and difficulties for clinical diagnosis to some extent; for example, low renin hypertension caused by the increase of other mineralocorticoids due to the inhibition of hereditary or acquired (from liquorice ingestion) 11-βHSD enzyme, pseudo-aldosteronism caused by the excessive consumption of liquorice, Cushing's syndrome, DOC secretion-producing tumors, and the like. These clinical symptoms are similar to PA, but are not PA, which causes lots of interference on the confirmed diagnosis of PA.

Therefore, it is urgent to find a more accurate kit for diagnosis, screening and typing as well as an integrated system of PA.

SUMMARY OF THE INVENTION

In view of the problems existing in the prior art, the present invention provides a screening kit and a confirmed and typing diagnosis system for primary aldosteronism. An object to be detected in a sample is extracted by a magnetic bead bonded with a balanced hydrophilic-lipophilic polymer on the surface thereof, and the content of the five markers of aldosterone, angiotensin I, angiotensin II, cortisol and 18-hydrocorticosterone in the sample is detected by liquid chromatography-tandem mass spectrometry for one time; an ARR value is calculated; an judgment is made in combination with a cut-off value of 20.4 of the ARR and a concentration of a hypertension therapeutic affecting the ARR value; when a positive result is judged, PA typing is performed according to the test values of the markers, thereby achieving the simultaneous detection of the content of the five markers such as, aldosterone on the same platform, and establishing the clinical cut-off value for the screening and confirmed diagnosis of PA, thus achieving the accurate diagnosis and typing of PA such that patients with hypertension secondary to PA can be screened and confirmed in early stage. Therefore, the present invention provides a reliable laboratory examination basis for clinicians to formulate an effective therapeutic intervention.

In one aspect, the present invention provides a detection kit for detecting primary aldosteronism; the kit includes an activating agent, a balanced solution, a washing liquid and an eluent solution; the activating agent is a solution including a magnetic bead with a surface, and a balanced hydrophilic-lipophilic polymer is bonded on the surface of the magnetic bead. The markers in a blood sample can be captured by the magnetic bead at one time; the marker is any one or more of aldosterone, angiotensin I, angiotensin II, cortisol and 18-hydrocorticosterone.

In this present invention, the content of a series of specific markers in a blood sample is detected accurately to provide good basis for the subsequent screening and typing. To achieve accurate detection, markers in the blood sample need to be accurately extracted firstly, and then combined with the following accurate detection, which may reflect the real content of each marker in the blood sample indeed.

The markers in the present invention include 5 types of aldosterone, angiotensin I, angiotensin II, cortisol and 18-hydrocorticosterone. The existing PA detection kits may be used to diagnose primary aldosteronism by detecting 3 markers at most only. The present invention innovates a one-step detection of 5 markers for the first time to achieve more accurate screening, confirmed and typing diagnosis of primary aldosteronism.

Directed to the detection of aldosterone and angiotensin I, this research group performed the detection originally in a way of pretreatment or single sample introduction; in the synchronous detection of three biomarkers of aldosterone, angiotensin I and angiotensin II, 96-well SPE plates (Agela PEP 96 Well Microplates) are used for extraction on a solid phase extraction column. After the SPE plate is activated and balanced, the biological sample solution to be detected is loaded on the SPE plate, and the target component is selectively extracted and adsorbed by a solid phase, and partial interference elements are washed off by drip washing, and then the target component is eluted from the extraction column with an eluting agent with a stronger binding capacity to the solid phase, thus achieving the purposes of separation and purification. The disadvantages are as follows: the operating steps, including activation, sampling, drip washing, and elution, are more tedious and time-consuming; a single batch of sample treatment takes two hours around. Moreover, the inter-well extraction efficiency of the sample greatly varies from the difference of the biological sample matrix; all the indexes need to be calibrated via isotope internal standards. Further, due to the specificity of the biological sample matrix, partial samples (in especial hemolysis, lipemia and other samples) may cause the blocking of the SPE column, leading to reduced pretreatment efficiency of the total batch of the sample and retest of the blocked sample. To further achieve the typing diagnosis of PA patients, new test indexes of 18-hydrocorticosterone and cortisol are added. Since both content and mass spectrum response of 18-hydrocorticosterone are lower, there is a higher demand for the enrichment efficiency and purification effect in the pretreatment process.

Therefore, dispersion solid phase extraction is used to treat samples. In the dispersion solid phase extraction, a solid absorbent material with specific adsorptive selectivity is dispersed into a biological sample solution, oscillated and mixed well such that the target component in the sample solution achieves a balance between the liquid phase and the selective adsorption solid phase. The dispersion solid phase extraction achieves the purpose of selective adsorption and extraction of the target markers according to the selectivity of the solid absorbent material. However, the major disadvantage is comparatively complex process of separating the solid phase from the solution.

To further solve the problem of the dispersion solid phase extraction, namely, too complex process of separating the solid phase from the solution, the magnetic bead with specific extraction and adsorption property is ultimately applied in this present invention to improve the separation process of the dispersion solid phase extraction. After the object to be detected is adsorbed by the magnetic bead specifically, the magnetic bead is extracted and transferred with a magnetic bead extractor. The present invention rapidly and efficiently achieves the steps such as, activation, drip washing, sampling, elution and waste discharge, overcomes the disadvantages of the above-mentioned extraction by an extraction column and the dispersion solid phase extraction, and greatly improves the automation efficiency of the pretreatment, effectively reduces the blocking of SPE column possibly caused by the specificity of the biological sample matrix and other problems. Moreover, the present invention reduces the matrix effects during the mass spectrometric detection of biological sample to shorten the pretreatment time of the same from 2 h to 10 min, and can further enhance the extraction effects of low-content indexes (aldosterone and 18-hydrocorticosterone) to improve the detection sensitivity.

Moreover, in terms of the solid phase extraction, different properties of polymer fillers are bonded on the surface of the solid phase, which will cause large impact on the adsorption and extraction effects of the object to be detected. Based on the search result of the literature on the single and separate detection of 5 different markers (the mixed anion exchange polymer SPE may be used in the sample pretreatment of the angiotensin detection), in this present invention, the solid phase extraction column bonded with a balanced hydrophilic-lipophilic polymer (Agela PEP 96 Well Microplates) filler is compared with the solid phase extraction column bonded a mixed anion exchange polymer (AgelaCleanert PAX 96 Wellplates) filler firstly. Through the comparison, it is found that the extraction effects of the solid phase extraction column bonded with a balanced hydrophilic-lipophilic polymer on the surface thereof on the 5 markers are not lower than those of the solid phase extraction column of the mixed anion exchange polymer, especially, it has better enrichment effect on the lower content of aldosterone and 18-hydrocorticosterone. Meanwhile, comparisons further are made to the magnetic bead bonded with a balanced hydrophilic-lipophilic polymer on the surface thereof, the magnetic bead bonded with a mixed anion exchange polymer and the magnetic bead bonded with a mixed cation exchange polymer. It is found that the magnetic bead bonded with a balanced hydrophilic-lipophilic polymer on the surface thereof has obvious advantages to improve the adsorption effects on the 5 markers. The reason is probably as follows: the balanced hydrophilic-lipophilic polymer may not only achieve the adsorption on high polar compounds, but also may effectively extract and adsorb the low polar compounds; but anionic and cationic polymers have stronger adsorptive selectivity and only selectively achieve the adsorption on high polar anions or cations, and hardly achieve the adsorption on low polar compounds simultaneously, leading to a low extraction efficiency of small molecules such as, aldosterone and 18-hydrocorticosterone, incapable of achieving the sensitivity requirements of clinical test.

A method for magnetic bead is applied. The magnetic bead bonded with a balanced hydrophilic-lipophilic polymer on the surface thereof is used to adsorb the 5 markers from a blood sample, and then a magnetic bead extractor may extract the magnetic bead which absorbs the markers from the biological sample matrix, thus effectively removing the interference elements from the biological sample. Therefore, after extraction and enrichment via the magnetic bead, compared with the solid phase extraction column, the eluent solution extracted by the magnetic bead has more purified components; the markers have smaller disturbing influences in the detection process; the mass spectrometry ionization efficiency is higher, and better detection sensitivity may be achieved. Moreover, the pretreatment process may achieve high degree of automation and a single batch of sample pretreatment only takes 10 min around.

To sum up, directed to the extraction of the 5 markers in the blood sample, a novel method for magnetic bead extraction is applied in this present invention, which may more adequately and efficiently extract the markers in a blood sample for one time. The magnetic bead is screened and pretreated. The magnetic bead bonded with a balanced hydrophilic-lipophilic polymer on the surface thereof is applied, which may selectively adsorb 5 markers with great differences in physical and chemical properties from the sample, thus achieving efficient extraction and accurate detection.

Further, the eluent solution is an aqueous solution containing 50% methanol.

After fully absorbing these markers for one time, the magnetic bead bonded with a balanced hydrophilic-lipophilic polymer on the surface thereof needs to be washed firstly, and then the target markers adsorbed areeluted, thus obtaining the content of each marker during the extraction of the blood sample.

In this present invention, research shows that when the aqueous solution containing 50% methanol is used as the eluent solution, the efficient elution of the 5 markers may be achieved, thus improving the sensitivity of the test results and effectively avoiding the solvent effect caused by too high concentration of organic phase content simultaneously.

Further, the washing liquid includes a washing liquid 1 and washing liquid 2; the washing liquid 1 is an aqueous solution with 10% methanol and the washing liquid 2 is isooctane.

Further, the activating agent is a solution of 50% ethanol including the magnetic bead, and the magnetic bead is a magnetic granule which is a core-shell solid phase and has a granularity of 30-50 μm, a specific surface area of 600 m$^2$/g and a pore diameter of 80 A.

Further, the present invention further contains a balanced solution and a liquid chromatogram mobile phase; the balanced solution is an aqueous solution with 1% formic acid.

Further, the liquid chromatogram mobile phase includes a mobile phase A and a mobile phase B; the mobile phase A is an aqueous solution containing an additive, and the mobile phase B is a methanol solution containing an additive (with 5% isopropanol).

Further, the additive is 1 mM ammonium fluoride.

The balanced solution can simply and rapidly wrap the magnetic bead bonded with a balanced hydrophilic-lipophilic polymer on the surface thereof, thus completing the improvement of the activity of the magnetic bead. Moreover, markers in the sample can be further wrapped by the balanced solution, thus enhancing the bonding of the magnetic bead to the markers more, and greatly improving the enrichment effect of the magnetic bead.

An additive, 1 mM ammonium fluoride, is added to the mobile phase, which is capable of significantly improving the detection sensitivity of the markers in the sample, especially for the ionization efficiency of a low content index, aldosterone.

In the other aspect, the present invention provides an application of a kit in the preparation of a screening, confirmed and typing diagnosis kit for primary aldosteronism; the kit includes an activating agent, a washing liquid and an eluent solution; the activating agent is a solution containing a magnetic bead, and a balanced hydrophilic-lipophilic polymer is bonded on the surface of the magnetic bead; the markers in a blood sample can be captured by the magnetic bead at one time, and the markers are aldosterone, angiotensin I, angiotensin II, cortisol and 18-hydrocorticosterone.

In a further aspect, the present invention provides a method for detecting markers in a blood sample; the method includes the following steps:

(1) treating the blood sample with a magnetic bead bonded with a balanced hydrophilic-lipophilic polymer on the surface thereof to absorb the markers in the blood sample;

(2) using an eluent solution to elute the markers from the magnetic bead and using a liquid chromatography tandem-mass spectrometry to test the numbers of the markers in the blood sample; the markers are aldosterone, angiotensin I, angiotensin II, cortisol and 18-hydrocorticosterone.

High performance liquid chromatography (HPLC)-tandem mass spectrometry is applied in this present invention to detect the 5 markers. The HPLC-tandem mass spectrometry has the advantages of high sensitivity and high specificity, and can achieve the combined detection of multiple clinical indexes in the same standard, thus reducing the result deviation caused by the difference between different detection systems and greatly improving the sensitivity and specificity in the diagnosis of secondary hypertension and other internal secretion-associated diseases.

Further, the blood sample in the step (1) firstly needs to be incubated in a buffer formation solution with an angiotensin converting enzyme inhibitor (PMSF) under acidic conditions, and at the end of the incubation, a stop buffer is added to stop the incubation, and then the incubated blood sample is treated(mixed or contacted) by the magnetic bead bonded with a balanced hydrophilic-lipophilic polymer on the surface thereof.

Further, the buffer formation solution has a pH value of 5-6.

During the incubation, angiotensinogen in the plasma sample will be converted into angiotensin I under the catalysis of renin activity, and due to the addition of the angiotensin converting enzyme inhibitor PMSF, the conversion of the angiotensin I into the angiotensin II is blocked. Renin activity is calculated by the change in the content of the angiotensin I.

During the incubation, the pH value of the sample must be controlled within a suitable scope, or, the catalytic activity of renin will be affected seriously, leading to a larger deviation in the angiotensin I generated after the incubation. The measured renin activity is low under nonideal pH conditions, and there is a false-positive result when ARR value is calculated by aldosterone/renin activity.

In some embodiments, the buffer formation solution has a pH value of 5.4-5.6.

In some embodiments, the pH value of the incubated blood sample is associated with the pH values of the buffer solution, the buffer formation solution, the stop buffer, diluting agent for the preparation of the sample, and the like.

In some embodiments, preferably, the buffer formation solution has a pH value of 5.5.

In some embodiments, the step (1) is as follows: adsorbing the blood sample with the magnetic bead that is treated by an activating agent and a balanced solution in order, and then washed with a washing liquid before using an eluent solution to elute the markers from the magnetic bead.

Further, the activating agent is a solution of 50% ethanol including the magnetic bead.

Further, the magnetic bead is a magnetic granule which is a core-shell solid phase and has a granularity of 30-50 μm, a specific surface area of 600 m$^2$/g and a pore diameter of 80 A.

Further, the balanced solution is an aqueous solution with 1% formic acid.

Further, the washing liquid includes a washing liquid 1 and a washing liquid 2; the washing liquid 1 is an aqueous solution with 10% methanol and the washing liquid 2 is isooctane.

Further, the eluent solution in the step (2) is an aqueous solution containing 50% methanol.

Further, the LC mobile phase in the step (2) includes a mobile phase A and a mobile phase B; the mobile phase A is an aqueous solution containing an additive, and the mobile phase B is a methanol solution containing an additive (with 5% isopropanol); the additive is 1 mM ammonium fluoride.

In a further aspect, the present invention provides a screening, confirmed and typing diagnosis system for primary aldosteronism; the system includes a marker test module, a data input/output interface and a data analysis module; the marker test module is used for testing a test value of each marker obtained by the above method; the data input/output interface is used for inputting a test value of each marker; the data analysis module is used for analyzing the test value of each marker; the markers are aldosterone, angiotensin I, angiotensin II, cortisol and 18-hydrocorticosterone; after the analysis of the data analysis module, the data input/output interface is used for outputting a screening, confirmed and typing diagnosis result of primary aldosteronism.

In the existing diagnostic process of PA, the quantitative determination of aldosterone is throughout the screening, confirmed and typing diagnosis. Aldosterone and renin activity are preferred biochemical indexes to screen PA; the confirmed test mainly replies on the quantitative results of aldosterone, and typing diagnosis relies on the reliable determination of aldosterone and cortisol more. The existing methods are chemiluminescent immunoassay or radioimmunoassay; there is no detection system capable of achieving simultaneous detection under the same standard.

The system provided by the present invention may be used to simultaneously detect 5 markers by HPLC-tandem mass spectrometry, and then complete the screening, confirmed and typing diagnosis of PA. The whole process is more efficient. Moreover, the system of the present invention has the advantages of high sensitivity, good specificity, quantitative and qualitative determination of interference drugs, and the like during the diagnosis and identification of primary aldosteronism, thus achieving more accurate and reliable screening and typing results.

Further, the method for analyzing the test value of the marker by the data analysis module is as follows: calculating ARR value based on aldosterone and renin activity and making a judgment in combination with a cut-off value of the ARR and a concentration of a hypertension therapeutic affecting the ARR value; when a positive result is judged, confirmed and typing diagnosis is performed according to the test values of the aldosterone, the angiotensin I, the angiotensin II, the cortisol and the 18-hydrocorticosterone; the renin activity is a yield of the angiotensin I per unit time.

Further, the ARR has a cut-off value of 20.4.

The cut-off value of ARR is commonly believed as 30 in the prior art. The cut-off value of ARR needs to be adjusted 20.4 when the screening, confirmed and typing diagnosis system for primary aldosteronism provided in the present invention is applied. Research shows that when the cut-off value of ARR is 20.4, the screening, confirmed and typing result has higher sensitivity and specificity, being 94.4% (95% CI:72.7-99.9) and 87.2% (95% CI: 72.6-95.7) respectively; Youden index is up to the maximum value (YI=0.82) and area under the curve (AUC) is up to 0.956.

This is mainly because the ARR value is directly correlated to the detection sensitivity of aldosterone and renin activity. Aldosterone is universally detected by chemiluminesent immunoassay previously, but the test value is higher such that the calculated result of the ARR value is greater than the actual value. Therefore, it needs to set a cut-off value of 30 to judge whether PA is positive or negative accurately more. When the sample pretreatment (extraction by the magnetic bead bonded with a balanced hydrophilic-lipophilic polymer) and detection method (HPLC-tandem mass spectrometry) provided by the present invention are applied, the test value may reflect the content of the aldosterone reagent more accurately. Therefore, the previous cut-off value of 30 of ARR has not conformed to the PA screening and typing system provided by the present invention; the cut-off value of ARR needs to be adjusted 20.4 such that the screening and typing result has a higher sensitivity, and the diagnostic result is more accurate.

In some embodiments, the calculation formula of the ARR is as follows: ARR=concentration of aldosterone/renin activity (production rate of angiotensin I); the renin activity is calculated by detecting the concentration of angiotensin I in the pre-incubation sample and in the post-incubation sample and according to the following formula: production rate of angiotensin I=(concentration of angiotensin I in the post-incubation sample—concentration of angiotensin I in the pre-incubation sample)/incubation time.

In some embodiments, the concentration of the pre-incubation angiotensin I is very low and thus, may be basically ignored.

In some embodiments, the binding affects the concentration of the ARR hypertension therapeutic for judgment, which is aimed at eliminating interference from the therapeutic. There are hundreds of drugs for the treatment of hypertension clinically. Drugs which will interfere the screening and diagnosis of PA are angiotensin converting enzyme (ACE) inhibitors (e.g., Perindopril and Captopril), angiotensin II receptor blocking agents (e.g., Losartan and Candesartan), calcium ion antagonists, β-receptor blocking agents, diuretics and the like. This is solved by the applicant in the patent invention 2021106374412 of the prior application, namely, how to eliminate the false-positive or false-negative drug interference. The PA screening and typing system of PA provided by the present invention needs to be combined with the method provided by the patent invention 2021106374412 to eliminate the drug interference.

In a further aspect, the present invention provides an application of the magnetic bead in extracting 5 markers in a blood sample simultaneously; the markers are aldosterone, angiotensin I, angiotensin II, cortisol and 18-hydrocorticosterone; a balanced hydrophilic-lipophilic polymer is bonded on the surface of the magnetic bead (HLB magnetic bead from Biosepur). The magnetic bead is a magnetic granule which is a core-shell solid phase and has a granularity of 30-50 µm, a specific surface area of 600 $m^2/g$ and a pore diameter of 80 A.

The screening kit, and the confirmed and typing diagnosis system for primary aldosteronism constructed in this present invention have the following beneficial effects:

1. The blood sample is treated with a magnetic bead bonded with a balanced hydrophilic-lipophilic polymer on the surface thereof to adsorb 5 markers in the blood sample more fully, thus achieving the accurate extraction and precise detection.

2. The extraction process of the magnetic bead is screened and optimized, and the pH value of the blood sample is adjusted; formic acid is added to the eluent solution and LC mobile phase; and suitable activating agent, balanced solution and washing liquid are chosen to greatly improve the enrichment and extraction effects of the magnetic bead and to achieve the efficient extraction of the 5 markers. Therefore, the amount of the markers extracted is closer to the real content of those in the blood sample, thus improving the accuracy of the test results.

3. The screening and typing diagnosis system for PA is established; the system has the advantages of high sensitivity, good specificity, quantitative and qualitative determination of interference drugs during the diagnosis and identification of primary aldosteronism, thus achieving more accurate and reliable screening, confirmed and typing results.

4. The cut-off value of ARR is adjusted 20.4 such that the screening and typing result has higher sensitivity and specificity, being 94.4% (95% CI:72.7-99.9) and 87.2% (95% CI: 72.6-95.7) respectively; Youden index is up to the maximum value (YI=0.82) and area under the curve (AUC) is up to 0.956.

5. The patients with hypertension secondary to PA can be screened and confirmed in early stage, which provides a reliable laboratory examination basis for clinicians to formulate effective therapeutic interventions.

DETAILED DESCRIPTION (1) Diagnosis or Detection

Diagnosis or detection here refers to test or assay on a biomarker in a sample, or on a content of a target biomarker, for example, an absolute content or a relative content, and then the presence or the amount of the target marker serves to indicate whether an individual providing the sample has or suffers from a certain disease, or has the possibility of a certain disease. The meaning of the diagnosis or detection here may be exchanged. The result of such detection or diagnosis may not be directly used as a direct result of a disease, but an intermediate result. If it is desired to obtain the direct result, pathological or anatomic or other auxiliary means is required to confirm whether patients suffer from a certain disease. For example, the present invention provides a plurality of novel biomarkers correlated to primary aldosteronism; the change of the content of these markers is directly correlated to the presence of primary aldosteronism.

(2) Correlation Between Markers or Biomarkers and PA

Markers or biomarkers have the same meanings in the present invention. The correlation here refers that the presence or content change of a certain biomarker in a sample is directly correlated to a specific disease, for example, the relative increase or decrease of the content indicates that the possibility of suffering from the disease is higher than that for healthy people.

If the plurality of different markers are present simultaneously or the content changes relatively in a sample, it indicates that the possibility of suffering from the disease is also higher than that for healthy people. That is, for the different types of markers, some markers are strongly correlated to the disease, while some markers are poorly correlated to the disease, or some are not correlated to a specific disease. One or more markers with strong correlation may be used as the markers for the diagnosis of a disease; the markers with weak correlation may be used to diagnose a certain disease in combination with the markers with strong correlation, thus improving the accuracy of the test results.

Since it has been found in the present invention that the series of markers in blood plasma are closely correlated to PA, and the series of markers can be detected for one time by high performance liquid chromatography (HPLC)-tandem mass spectrometry, which is jointly useful for the screening, confirmed and typing diagnosis of PA.

BRIEF DESCRIPTION OF DRAWINGS

FIG. 1A-FIG. 1E are test chromatogram of 5 markers in a blood sample provided in Example 1 and wherein FIG. 1A is the chromatogram of angiotensin I; FIG. 1B is the chromatogram of angiotensin II; FIG. 1C is the chromatogram of 18OH—Corticosterone;; FIG. 1D is the chromatogram of aldosterone ; FIG. 1E is the chromatogram of Cortisol.

DETAILED DESCRIPTION OF THE INVENTION

Figure 1A:
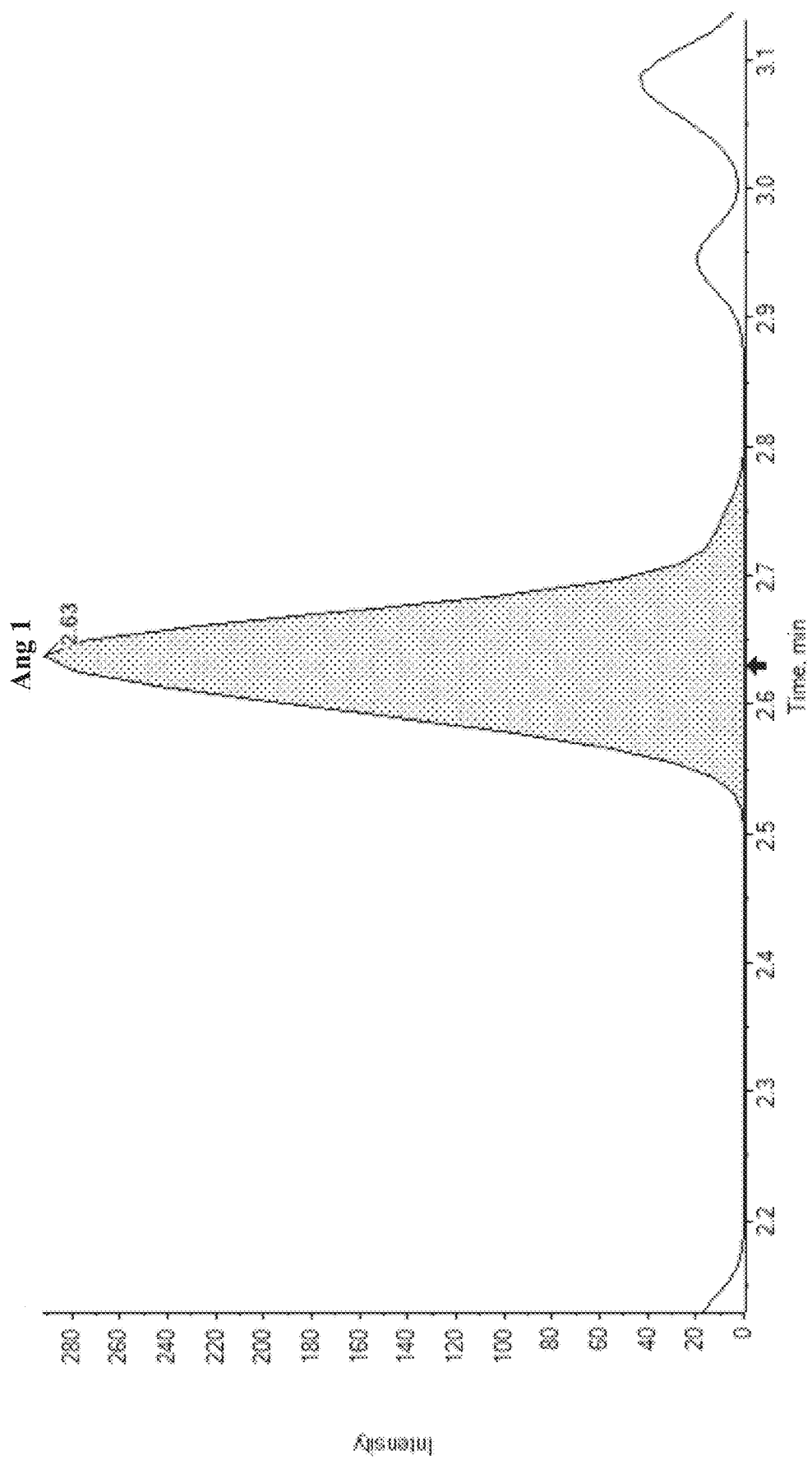
Figure 1B:
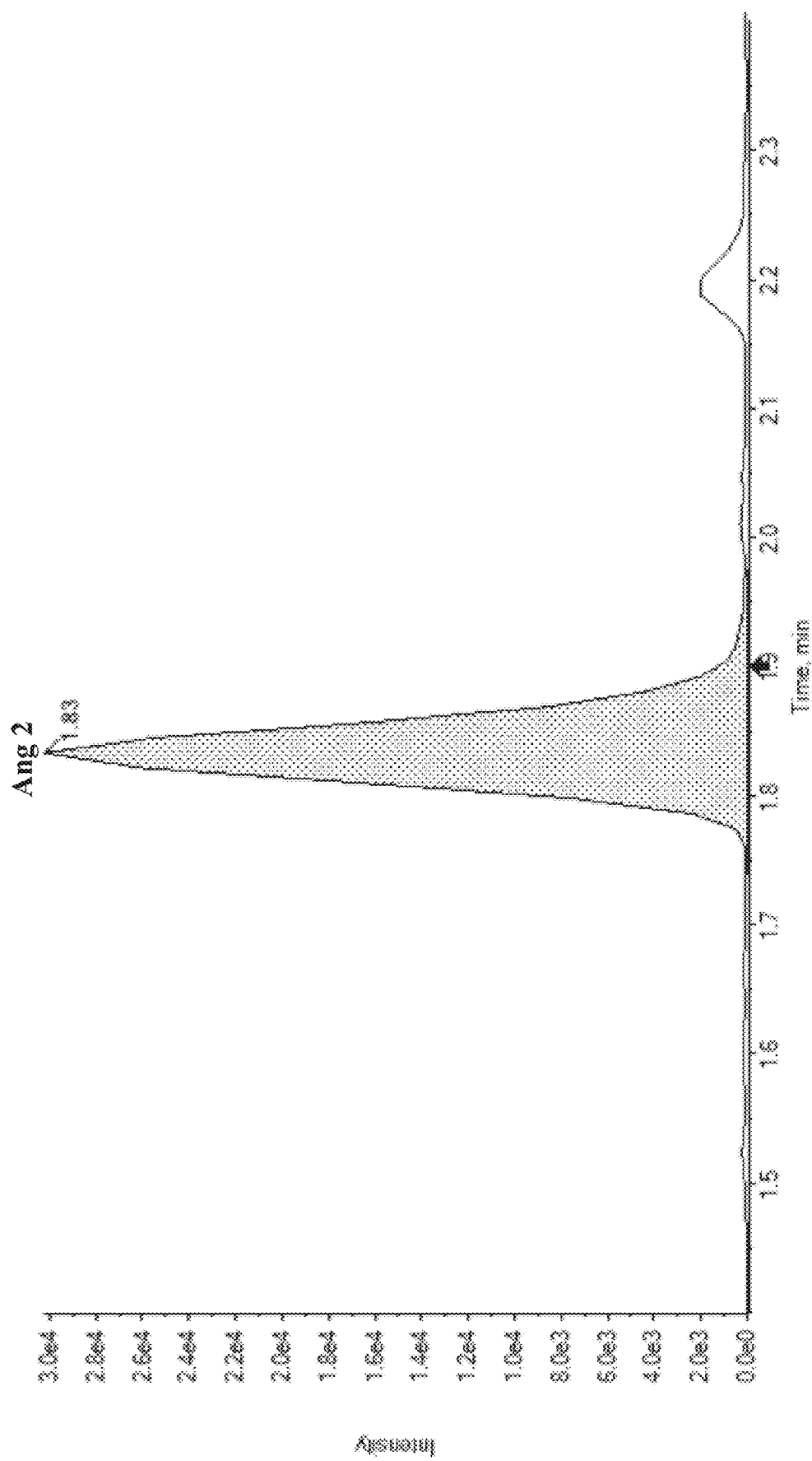
Figure 1C:
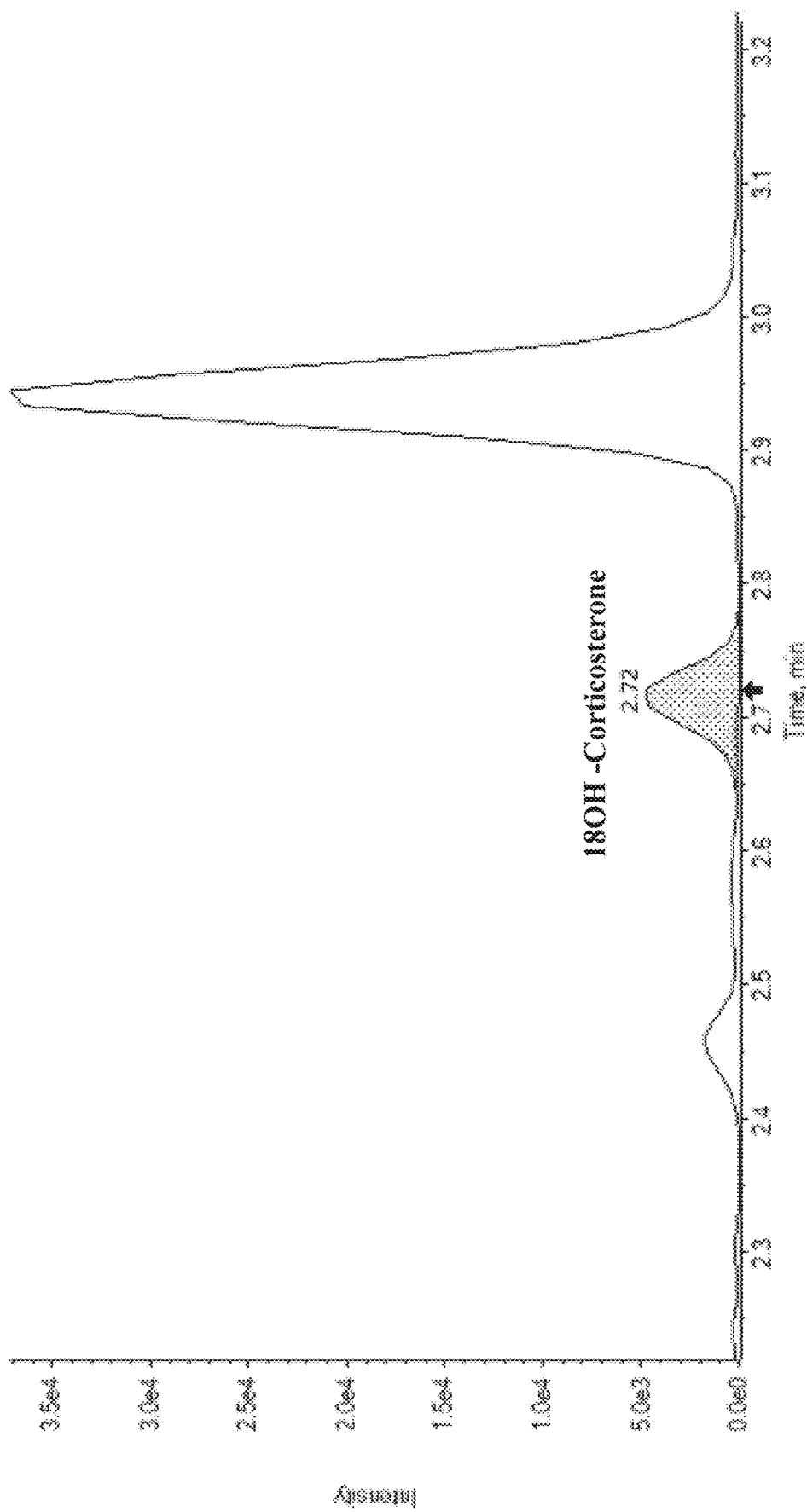
Figure 1D:
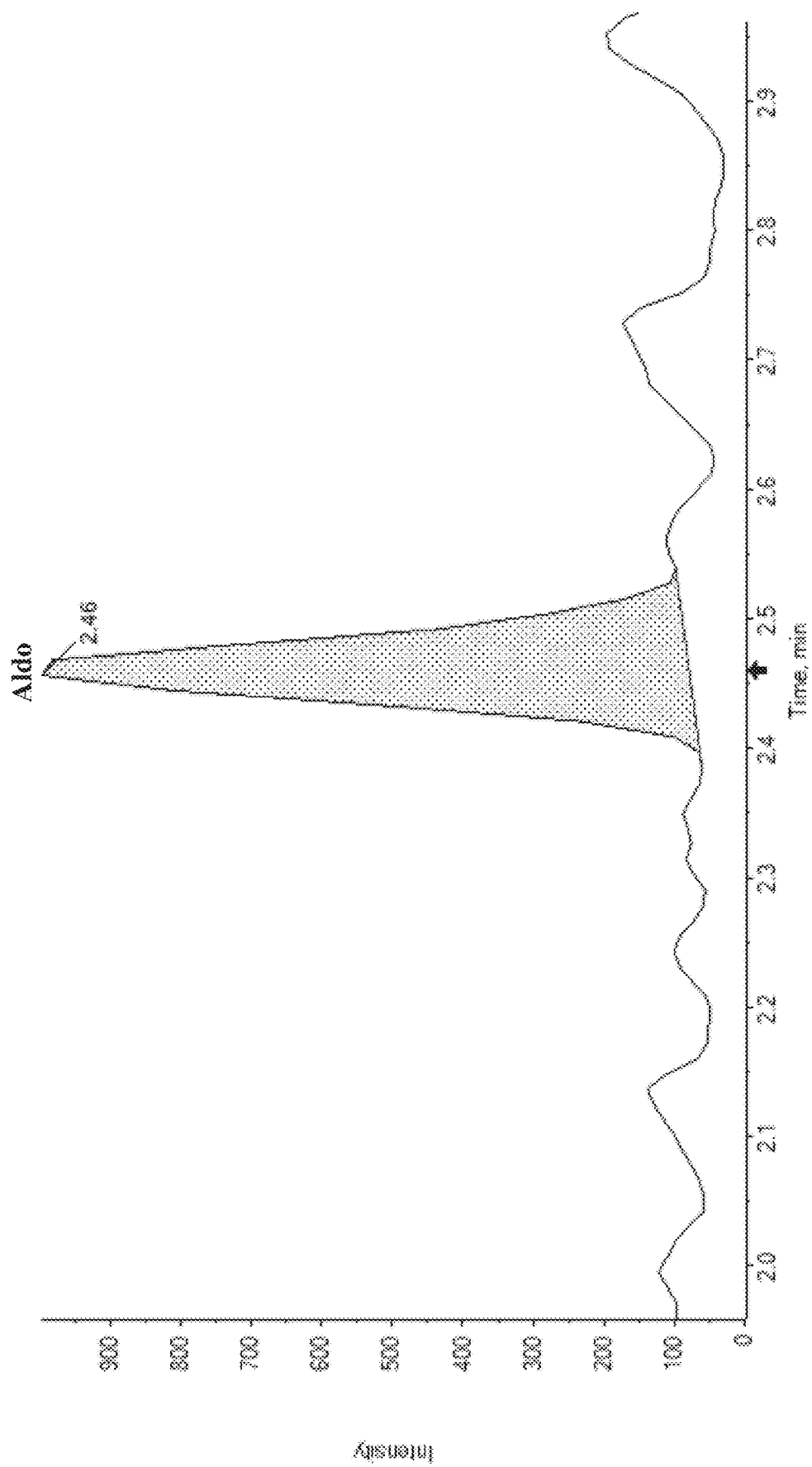
Figure 1E:
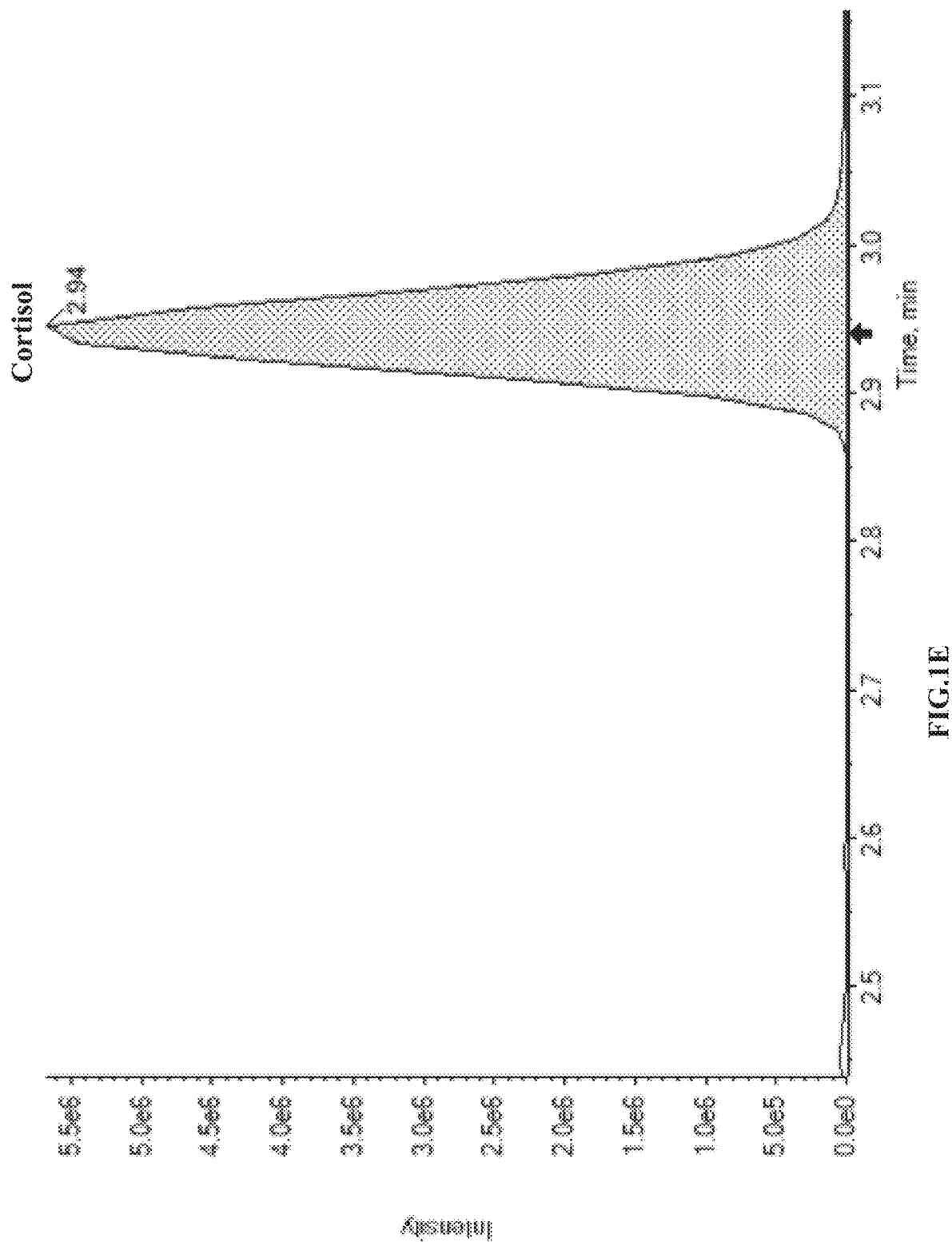

To describe the present invention more specifically, the technical solutions of the present invention will be described in detail with reference to the accompanying drawings and detailed embodiments. The description merely indicates how the present invention is achieved, but is not construed as limiting the specific scope of the present invention. The scope of the present invention is defined by the claims.

Example 1: Accurate Detection of Each Marker

I. Solution Preparation

Preparation of the mixed working solution of a calibration product and a quality control product is shown in Table 1:

TABLE 1

Preparation of the mixed working solution of a calibration product and a quality control product

| Analyte | Concentration of the primary stock solution mg/ml | Volume μl | Volume of the aqueous solution of 50% methanol μl | Concentration of the secondary stock solution mg/ml | Volume μl | Volume of the aqueous solution of 50% methanol μl | Concentration of the mixed working solution μg/ml |
|---|---|---|---|---|---|---|---|
| Angiotensin I | 1 | 100 | 900 | 100 | 50 | 675 | 5 |
| Angiotensin II | 1 | 10 | 990 | 10 | 25 | | 0.25 |
| Aldosterone | 1 | 10 | 990 | 10 | 25 | | 0.25 |
| Cortisol | 1 | — | — | 1000 | 25 | | 25 |
| 18-hydro-corticosterone | 0.1 | 100 | 900 | 10 | 20 | | 0.2 |

Preparation and Concentration Gradient of the Calibration Product are Shown in Table 2:

TABLE 2

Preparation of the calibration product

| pg/ml | Name of the working solution | Volume of the working solution μL | Volume of matrix μL | Ang I (ng/mL) | Ang II (pg/mL) | Aldosterone (pg/ml) | Cottisol (ng/mL) | 18OH-Corticosterone (pg/ml) |
|---|---|---|---|---|---|---|---|---|
| LLMI | Calibration product S5 | 15 | 985 | 0.3 | 15 | 15 | 1.5 | 12 |
| Calibration product S1 | Calibration product S5 | 15 | 985 | 0.3 | 15 | 15 | 1.5 | 12 |
| Calibration product S2 | Calibration product S5 | 37.5 | 962.5 | 0.75 | 37.5 | 37.5 | 3.75 | 30 |
| Calibration product S3 | Calibration product S7 | 15 | 985 | 1.5 | 75 | 75 | 7.5 | 60 |
| Calibration product S4 | Calibration product S7 | 50 | 950 | 5 | 250 | 250 | 25 | 200 |
| Calibration product S5 | Calibration product S7 | 200 | 800 | 20 | 1000 | 1000 | 100 | 800 |
| Calibration product S6 | Mixed working solution | 10 | 990 | 50 | 2500 | 2500 | 250 | 2000 |
| Calibration product S7 | Mixed working solution | 20 | 980 | 100 | 5000 | 5000 | 500 | 4000 |

Note:
the matrix for the preparation of the calibration product is a PBS (1X) buffer solution containing 4% BSA, stored at 2-8° C.

Preparation of the quality control product is shown in Table 3:

TABLE 3

Preparation of the quality control product

|  | Name of the working solution | Name of the working solution | Volume of the working solution µL | Name of matrix | Volume of matrix µl |
|---|---|---|---|---|---|
| Preparation product of the quality control | Quality control product L | Calibration product S5 | 20 | Plasma | 980 |
|  | Quality control product M | Quality control product H | 100 | Quality control product L | 1100 |
|  | Quality control product H | Mixed working solution | 6.6 | Quality control product L | 993.4 |

Note:
the matrix of the quality control product is blood plasma which is subpackaged and frozen immediately after being prepared.

Preparation of the internal standard working solution is shown in Table 4:

TABLE 4

Preparation of the internal standard working solution

| Analyte | Concentration of the primary stock solution mg/ml | Volume µl | Volume of the aqueous solution with 50% methanol µl | Concentration of the secondary stock solution mg/ml | Volume µl | Volume of the aqueous solution with 50% methanol µl | Concentration of the mixed internal standard working solution ng/ml |
|---|---|---|---|---|---|---|---|
| Angiotensin I-IS | 0.1 | 100 | 900 | 10 | 50 | 10000 | 50 |
| Angiotensin II-IS | 0.1 | 10 | 990 | 1 | 25 |  | 2.5 |
| Aldosterone-d7 | 0.1 | 10 | 990 | 1 | 25 |  | 2.5 |
| Cortisol-d4 | 1 | 100 | 900 | 100 | 20 |  | 200 |
| 18-hydrocorticosterone-d4 | 0.1 | 100 | 900 | 1 | 25 |  | 2.5 |

Preparation of Other Solution

Preparation of phenylmethylsulfonyl fluoride (PMSF): 0.174 g PMSF was taken and added to 10 mL methanol and prepared into a 100 mM PMSF methanol solution; storage condition was 2-8° C.

Buffer formation solution: 12.11 g TRIS and 7.4 g ethylene diamine tetraacetic acid (EDTA) were added to a 100 mL volumetric flask, and added with deionized water to 90 mL, and then subjected to ultrasonic treatment for 30 min to be evenly dissolved. Deionized water was added to the scale line and mixed well. The solution was transferred to a reservoir vessel made of polypropylene. The PH value of the solution was adjusted within 5.45-5.60, and then the solution was stored at −20° C.

Buffer formation solution A: the solution was prepared at the same day of the detection analysis; 100 µL of 100 mM PMSF (angiotensin converting enzyme inhibitor) solution was added to 10 mL of the buffer formation solution, thus preparing the buffer formation solution A (pH value ranges from 5.4 to 5.6).

Stop buffer containing internal standard: 1 mL of the internal standard working solution was mixed with 9 mL water and 250 µL formic acid into the stop buffer containing internal standard.

II. Sample Pretreatment

1. Sample thawing: a plasma sample to be tested and a quality control sample to be tested were placed into ice water (0° C.) for thawing till melted.

2. Sampling: 50 µL of the buffer formation solution A was added to a 96-well plate, and 400 µL of the calibration product, quality control product and quality control sample to be tested were taken and added to two plates prepared in the step (1), and then the remaining sample was immediately frozen.

3. Sample incubation: the sample in the step 2 was sealed with a silicone pad and subjected to vortex treatment for a short period of time, and then put to a 37° C. water bath for 3 h, 3 h later, 400 µL of the stop buffer containing internal standard was added, and the mixed solution was centrifuged for 1 min at 4° C. and 4000 rpm; 800 µL supernatant was taken and added to an automatic magnetic bead extractor, ready for sample extraction.

4. Magnetic bead extraction: additives of each column in the adaptive 96-well plate of the magnetic bead extractor are shown in Table 5:

TABLE 5

Additives of each column in the adaptive 96-well plate of the magnetic bead extractor

| First column (7) | Second column (8) | Second column (9) | Fourth column (10) | Fifth column (11) | Sixth column (12) |
|---|---|---|---|---|---|
| Activating agent | Balanced solution | Sample | Washing liquid 1 | Washing liquid 2 | Eluent solution |
| Activating agent | Balanced solution | Sample | Washing liquid 1 | Washing liquid 2 | Eluent solution |
| Activating agent | Balanced solution | Sample | Washing liquid 1 | Washing liquid 2 | Eluent solution |
| Activating agent | Balanced solution | Sample | Washing liquid 1 | Washing liquid 2 | Eluent solution |
| Activating agent | Balanced solution | Sample | Washing liquid 1 | Washing liquid 2 | Eluent solution |
| Activating agent | Balanced solution | Sample | Washing liquid 1 | Washing liquid 2 | Eluent solution |
| Activating agent | Balanced solution | Sample | Washing liquid 1 | Washing liquid 2 | Eluent solution |
| Activating agent | Balanced solution | Sample | Washing liquid 1 | Washing liquid 2 | Eluent solution |

The magnetic bead is the magnetic bead bonded with a balanced hydrophilic-lipophilic polymer on the surface thereof (Biosepur, Art.No.: BNMA7300001-0; granularity: 30-50 μm; specific surface area: 600 $m^2/g$ and pore diameter: 80 Å). The activating agent is a solution of 50% ethanol including the magnetic bead; the balanced solution is an aqueous solution containing 1% formic acid; the washing liquid 1 is an aqueous solution containing 10% methanol; the washing liquid 2 is isooctane, and the eluent solution is an aqueous solution containing 50% methanol.

5. The sample pretreatment step of the magnetic bead extractor is shown in Table 6; the pretreatment time of each batch of samples is about 10 min.

TABLE 6

Sample pretreatment step of the magnetic bead extractor

| No. | Instruction | Columns of the 96-well plate | Mixing time (S) | Solvent amount (μl) | Magnetic absorption time (S) |
|---|---|---|---|---|---|
| 1 | Activating | 1 (7) | 60 | 300 | 30 |
| 2 | Activating | 2 (8) | 60 | 300 | 30 |
| 3 | Sampling | 3 (9) | 90 | 800 | 30 |
| 4 | Drip washing | 4 (10) | 60 | 300 | 30 |
| 5 | Drip washing | 5 (11) | 60 | 300 | 30 |
| 6 | Eluting | 6 (12) | 60 | 100 | 30 |
| 7 | Waste discharge | 1 (7) | 10 | 100 | 0 |

6. After the extraction was completed by the magnetic bead extractor, the solution to be tested in the columns 6 and 12 of the 96-well plate was transferred to the 96-well loading plate for detection on the machine. The existing magnetic bead extractor may accommodate two 96-well plates for parallel operation for one time. Therefore, the pretreatment flux is 32 samples/batch; a 96-channel magnetic bead extractor may be also available; and the extraction steps are kept same.

III. Sample Detection

In the process of the liquid chromatography tandem-mass spectrometry, gradient elution was applied in the liquid chromatography; separation conditions of the object to be detected for the reversed phase chromatography were established as follows: chromatographic column was a Phenomenex C8 chromatographic column; flow rate was 0.4 mL/min; column temperature was 40° C.; where the mobile phase A was an aqueous solution containing 1 mM ammonium fluoride, and the mobile phase B was a methanol solution containing 1 mM ammonium fluoride (with 5% isopropanol); the volume ratio of the mobile phase A to the mobile phase B was 90-5%:10-95%. The gradient elution program is shown in Table 7.

TABLE 7

Gradient elution program

| Time (min) | Flow rate (mL/min) | Mobile phase A (%) | Mobile phase B (%) |
|---|---|---|---|
| 0 | 0.4 | 80 | 20 |
| 0.3 | 0.4 | 80 | 20 |
| 0.6 | 0.4 | 50 | 50 |
| 3.3 | 0.4 | 50 | 50 |
| 3.4 | 0.4 | 5 | 95 |
| 4.2 | 0.4 | 5 | 95 |
| 4.3 | 0.4 | 80 | 20 |
| 4.8 | 0.4 | 80 | 20 |

During the mass spectrometric detection, quantitative detection was performed by a triple quadrupole mass spectrometer with a model of CalQuant-S independently developed and researched by CALIBAR. The mass spectrometry was performed by a positive/negative ion mode (ESI+) of an ESI source and a multi-reaction monitoring MRM mode. The corresponding mass spectrometry is shown in Table 8, and the mass spectrometry conditions are shown in Table 9:

TABLE 8

Mass spectrometry

| Q1 | Q3 | DWELL | ID | DP | CE | CXP |
|---|---|---|---|---|---|---|
| 433.1 | 619.2 | 30 | Angiotensin I-1 | 139 | 30 | 8 |
| 433.1 | 647.4 | 5 | Angiotensin I-2 | 145 | 25 | 7 |
| 437.3 | 660.5 | 30 | Angiotensin I-IS-2 | 120 | 24 | 16 |
| 437.3 | 631.1 | 5 | Angiotensin I-IS-2 | 130 | 30 | 10 |
| 523.9 | 263.4 | 30 | Angiotensin II-1 | 140 | 31 | 7 |
| 523.9 | 784.3 | 5 | Angiotensin II-2 | 140 | 28 | 8 |
| 527.3 | 263.3 | 30 | Angiotensin II-IS-1 | 140 | 31 | 7 |
| 527.3 | 791.4 | 5 | Angiotensin II-IS-2 | 140 | 28 | 7 |
| 363.3 | 121.1 | 10 | 18-hydrocorticosterone-1 | 140 | 40 | 10 |
| 363.3 | 269.2 | 10 | 18-hydrocorticosterone-2 | 140 | 38 | 10 |
| 367.2 | 121.1 | 10 | 18-hydrocorticosterone-IS-1 | 140 | 40 | 10 |
| 367.2 | 273.2 | 10 | 18-hydrocorticosterone-IS-2 | 140 | 38 | 10 |
| 359.2 | 188.9 | 25 | Aldosterone-NEG-1 | −125 | −26 | −8 |
| 359.2 | 331.3 | 10 | Aldosterone-NEG-2 | −125 | −23 | −8 |
| 367.2 | 194.2 | 25 | Aldosterone-NEG-IS-1 | −125 | −26 | −8 |
| 367.2 | 339.4 | 10 | Aldosterone-NEG-IS-2 | −125 | −23 | −8 |
| 363.2 | 309.2 | 30 | Cortisol-1 | 175 | 25 | 8 |
| 363.2 | 121.2 | 15 | Cortisol-2 | 175 | 32 | 8 |
| 367.2 | 313.3 | 30 | Cortisol-IS-1 | 175 | 25 | 8 |
| 367.2 | 121.2 | 15 | Cortisol-IS-2 | 175 | 32 | 8 |

TABLE 9

Mass spectrometry conditions

| Mass spectrometry conditions | Value |
|---|---|
| Curtain gas CUR | 25 psi |
| Atomized gas GS1 | 55 psi |
| Auxiliary heating gas GS2 | 55 psi |
| Ion source heating temperature | 500° C. |
| Collision gas CAD | 10 psi |
| Spray voltage | 5500 V/−4500 V |

A standard curve was established by the internal standard method. Records of validation on the linear relation is shown in Table 10 with a measuring unit of ng/mL.

TABLE 10

Results of validation on the standard curve

| Compound | Regression equation | Weight | Coefficient of association r | Clinical linear range |
|---|---|---|---|---|
| Angiotensin I | Y = 0.00957X + 0.000836 | $1/X^2$ | 0.997 | 0.3-100 ng/ml |
| Angiotensin II | Y = 0.0000762593X + 0.00303 | $1/X^2$ | 0.996 | 15-5000 pg/ml |
| Aldosterone | Y = 0.00250X − 0.03029 | $1/X^2$ | 0.997 | 15-5000 pg/ml |
| Cortisol | Y = 0.04826X + 0.13974 | $1/X^2$ | 0.998 | 1.5-500 ng/ml |
| 18-hydrocorticosterone | Y = 0.000956X + 0.07801 | $1/X^2$ | 0.999 | 12-4000 pg/ml |

The standard curve was formulated by the PBS buffer solution matrix containing 4% BSA and subjected to synchronous treatment with the sample to be tested for detection. The test chromatogram is shown in FIG. 1, representing angiotensin I (Ang I), angiotensin II (Ang II), 18-hydrocorticosterone (18-OH CORT), aldosterone (Aldo) and Cortisol from top to bottom in order. As can be seen from FIG. 1, the method provided by the example may accurately detect the 5 markers simultaneously.

By the validation on accuracy and precision (Table 11), the detection linear relation is good within the scope of concentration.

TABLE 11

Accuracy and precision validated by the method

| Compound | Sample size | Theoretical concentration | Measured value | Accuracy | Imprecision |
|---|---|---|---|---|---|
| Angiotensin I | 6 | 1.8 ng/ml | 1.79 ng/ml | 99.44% | 2.50% |
| | | 4.8 ng/ml | 4.81 ng/ml | 100.2% | 2.08% |
| | | 34.8 ng/ml | 34.5 ng/ml | 99.13% | 1.58% |
| Angiotensin II | 6 | 50 pg/ml | 49.3 pg/ml | 98.60% | 1.42% |
| | | 200 pg/ml | 198 pg/ml | 99.00% | 3.08% |
| | | 1700 pg/ml | 1702 pg/ml | 100.1% | 2.12% |
| Aldosterone | 6 | 50 pg/ml | 50.3 pg/ml | 100.6% | 3.00% |
| | | 200 pg/ml | 198 pg/ml | 99.20% | 3.47% |
| | | 1700 pg/ml | 1693 pg/ml | 90.58% | 1.13% |
| Cortisol | 6 | 50 ng/ml | 50.7 ng/ml | 101.40% | 2.46% |
| | | 65 ng/ml | 65.6 ng/ml | 100.92% | 1.12% |
| | | 215 ng/ml | 214 ng/ml | 99.53% | 3.46% |
| 18-hydrocorticosterone | 6 | 160 pg/ml | 159 pg/ml | 99.38% | 2.38% |
| | | 280 pg/ml | 289 pg/ml | 104% | 2.01% |
| | | 1480 pg/ml | 1489 pg/ml | 100.6% | 3.20% |

Example 2: Comparison of the Extraction Effect Between the Magnetic Bead Bonded with a Balanced Hydrophilic-Lipophilic Polymer and the Solid Phase Extraction Column The preparation, extraction and detection of the sample at the minimum concentration point (S1) of the standard curve were performed by the method provided in Example 1. The extraction was performed respectively by the different three methods: 1, extraction by the magnetic bead bonded with a balanced hydrophilic-lipophilic polymer on the surface thereof (HLB magnetic bead, Biosepur, Art.No.: BNMA7300001-0; granularity: 30-50 μm; specific surface area: 600 $m^2$/g and pore diameter: 80A); 2, extraction by PEP 96 Well Microplates of the SPE plate filled with a balanced hydrophilic-lipophilic polymer; 3, extraction by PEP 96 Waters Oasis HLB of the SPE plate filled with a balanced hydrophilic-lipophilic polymer; after elution, the sample was subjected to liquid chromatography tandem-mass spectrometry; the test result of the treated sample was surveyed to measure the peak areas of the 5 markers in the sample S1, as shown in Table 12.

TABLE 12

Effects of different treatment methods on the extraction effects of the markers

| Marker/Treatment method | | HLB magnetic bead | PEP 96 Well Microplates | Waters Oasis HLB 96 Wellplates |
|---|---|---|---|---|
| Angiotensin I (theoretical concentration: 0.3 ng/ml) | Peak area | 6460 | 5876 | 5031 |
| Angiotensin II (theoretical concentration: 15 pg/ml) | Peak area | 8967 | 7462 | 7270 |
| Aldosterone (theoretical concentration: 15 pg/ml) | Peak area | 4563 | 3687 | 3852 |
| Cortisol (theoretical concentration: 1.5 ng/ml) | Peak area | 163653 | 14573 | 14135 |
| 18-Hydrocorticosterone (theoretical concentration: 12 pg/ml) | Peak area | 1019 | 821 | 820 |

As can be seen from Table 12, different sample treatment methods will affect the extraction results of the 5 markers in the sample; compared with the SPE plate embedded the balanced hydrophilic-lipophilic polymer, the magnetic bead has more significant extraction effect on the 5 markers. Meanwhile, the two SPE plates of balanced hydrophilic-lipophilic polymer are compared, and there is a difference in effects to some extent; PEP 96 Well Microplates of the SPE plate are superior to the Waters Oasis HLB 96 Wellplates; compared with the two SPE plates, the HLB magnetic bead has significantly improved extraction effect on the 5 markers.

Moreover, the solid phase extraction is featured by easy blocking, complex operation and too stronger matrix effect, and the like. Therefore, the method of magnetic bead is applied. The magnetic bead bonded with a balanced hydrophilic-lipophilic polymer on the surface thereof is used to adsorb the 5 markers, and then the magnetic bead extractor may extract the magnetic bead which absorbs the markers from the biological sample matrix, thus effectively removing the interference elements in the biological sample. Therefore, after extraction and enrichment of the magnetic bead, compared with the solid phase extraction column, the eluent solution extracted by the magnetic bead has more purified components; the markers have smaller disturbing influences in the detection process; the mass spectrometry ionization efficiency is higher, and better detection sensitivity may be achieved.

Example 3: Effects of the Magnetic Bead Bonded Different Polymer Materials on the Extraction Effects of the Markers In this example, the preparation, extraction and detection of the sample at the minimum concentration point (S1) of the standard curve were performed by the method provided in Example 1. Based on the search result of the literature on the single and separate detection of the 5 different markers: the mixed anion exchange polymer SPE may be used in the sample pretreatment of the angiotensin detection. Therefore, comparisons were further made on the solid phase extraction column bonded a mixed anion exchange polymer (Agela-Cleanert PAX 96 Wellplates) filler, the magnetic bead bonded with a balanced hydrophilic-lipophilic polymer on the surface thereof (HLB magnetic bead, Biosepur, Art.No.: BNMA7300001-0; granularity: 30-50 μm; specific surface area: 600 m$^2$/g and pore diameter: 80 A), the magnetic bead bonded a mixed anion exchange polymer (MAX magnetic bead, Biosepur, Art.No.: BNMA1430-SY; granularity: 30-50 μm; specific surface area: 600 m$^2$/g and pore diameter: 80 A), and the magnetic bead bonded a mixed cation exchange polymer (MCX magnetic bead, Biosepur, Art.No.: BNMA8300001-0-P; granularity: 30-50 μm; specific surface area: 600 m$^2$/g and pore diameter: 80 A) in this example. The 5 markers were adsorbed and extracted in the 4 ways, and after elution, the sample was subjected to liquid chromatography tandem-mass spectrometry; the test result of the treated sample was surveyed to measure the peak areas of the 5 markers in the sample S1, as shown in Table 13.

TABLE 13

Effects of the magnetic bead bonded different materials on the extraction effects of the markers

| Marker/Magnetic bead bonding material | | Cleanert PAX 96 Wellplates | HLB magnetic bead | MAX magnetic bead | MCX magnetic bead |
|---|---|---|---|---|---|
| Angiotensin I (theoretical concentration: 0.3 ng/ml) | Peak area | 4961 | 6460 | 5261 | 4884 |
| Angiotensin II (theoretical concentration: 15 pg/ml) | Peak area | 7230 | 8967 | 7241 | 7067 |
| Aldosterone (theoretical concentration: 15 pg/ml) | Peak area | 2134 | 4563 | 4134 | 3242 |
| Cortisol (theoretical concentration: 1.5 ng/ml) | Peak area | 145467 | 163653 | 145349 | 148580 |
| 18-Hydrocorticosterone (theoretical concentration: 12 pg/ml) | Peak area | 382 | 1019 | 682 | 666 |

As can be seen from Table 13, in the same way of being bonded the anionic polymer, the extraction effect of the MAX magnetic bead is obviously superior to that of the AgelaCleanert PAX 96 Wellplates solid phase extraction column; meanwhile, different materials are bonded on the surface of the magnetic bead, which has a large impact on the extraction effects of the 5 markers in the blood sample. Comparisons are made on the magnetic beads bonded the three fillers of the hydrophilic-lipophilic polymer, the mixed anion exchange polymer and the mixed cation exchange polymer; among them, the magnetic bead bonded the hydrophilic-lipophilic polymer may significantly improve the extraction effect on a portion of low-content indexes (aldosterone and 18-hydrocorticosterone) and may achieve better balance on the extraction and enrichment effects of the 5 markers with greater differences in physical and chemical properties. The reason is probably as follows: the balanced hydrophilic-lipophilic polymer may not only achieve the adsorption on high polar compounds, but also may effectively adsorb the low polar compounds; but anionic and cationic polymers have stronger adsorptive selectivity and thus, only selectively achieve the adsorption on high polar anions or cations, and hardly achieve the adsorption on low polar compounds simultaneously, leading to a low extraction efficiency of small molecules such as, aldosterone and 18-hydrocorticosterone, incapable of achieving the sensitivity requirements of clinical test.

Example 4: Comparison of the Extraction Process Between the Magnetic Bead and the Solid Phase Extraction Column When a biological sample was pretreated by the conventional solid phase extraction column, the 96-well SPE plate (Agela PEP 96 Well Microplates) was firstly extracted by the solid phase extraction column for activation and balance, and then the biological sample solution to be tested was loaded on the SPE plates; the target compound was extracted and adsorbed by a PEP filler selectively; a portion of inorganic salt and other impurities were washed from the SPE column via drip washing, and then the target component was eluted from the extraction column by an eluting agent with stronger binding capacity to the solid phase, afterwards, the eluent solution was blown-dried with nitrogen gas, redissolved and loaded for sample detection. The operation process has more manual steps, is complex and time-consuming; it takes about 2 h to treat a batch of samples. Moreover, the inter-well extraction efficiency of the sample greatly varies from the difference of the biological sample matrix; all the indexes need to be calibrated via isotope internal standards. Further, due to the specificity of the biological sample matrix, partial samples (in especial hemolysis, lipemia and other samples) may cause the blocking of the SPE column, leading to reduced pretreatment efficiency of the total batch of the samples and retest of the blocked sample.

Additives of each column in the adaptive 96-well plate of the magnetic bead extractor are shown in Table 14 (the same as Table 5 above):

TABLE 14

Additives of each column in the adaptive 96-well plate of the magnetic bead extractor

| First column (7) | Second column (8) | Second column (9) | Fourth column (10) | Fifth column (11) | Sixth column (12) |
|---|---|---|---|---|---|
| Activating agent | Balanced solution | Sample | Washing liquid 1 | Washing liquid 2 | Eluent solution |
| Activating agent | Balanced solution | Sample | Washing liquid 1 | Washing liquid 2 | Eluent solution |
| Activating agent | Balanced solution | Sample | Washing liquid 1 | Washing liquid 2 | Eluent solution |
| Activating agent | Balanced solution | Sample | Washing liquid 1 | Washing liquid 2 | Eluent solution |
| Activating agent | Balanced solution | Sample | Washing liquid 1 | Washing liquid 2 | Eluent solution |
| Activating agent | Balanced solution | Sample | Washing liquid 1 | Washing liquid 2 | Eluent solution |
| Activating agent | Balanced solution | Sample | Washing liquid 1 | Washing liquid 2 | Eluent solution |
| Activating agent | Balanced solution | Sample | Washing liquid 1 | Washing liquid 2 | Eluent solution |

The magnetic bead is the magnetic bead bonded with a balanced hydrophilic-lipophilic polymer on the surface thereof (HLB magnetic bead, Biosepur, Art.No.: BNMA7300001-0; granularity: 30-50 μm; specific surface area: 600 m$^2$/g and pore diameter: 80 A). The activating agent is a solution of 50% ethanol including the magnetic bead; the balanced solution is an aqueous solution containing 1% formic acid; the washing liquid 1 is aqueous solution containing 10% methanol; the washing liquid 2 is isooctane, and the eluent solution is an aqueous solution containing 50% methanol.

The sample pretreatment step of the magnetic bead extractor is shown in Table 15 (the same as Table 6); the pretreatment time of each batch of samples is about 10 min.

TABLE 15

Sample pretreatment step of the magnetic bead extractor

| No. | Instruction | Columns of the 96-well plate | Mixing time (S) | Solvent amount (μl) | Magnetic absorption time (S) |
|---|---|---|---|---|---|
| 1 | Activating | 1 (7) | 60 | 300 | 30 |
| 2 | Activating | 2 (8) | 60 | 300 | 30 |
| 3 | Sampling | 3 (9) | 90 | 800 | 30 |
| 4 | Drip washing | 4 (10) | 60 | 300 | 30 |
| 5 | Drip washing | 5 (11) | 60 | 300 | 30 |
| 6 | Eluting | 6 (12) | 60 | 100 | 30 |
| 7 | Waste discharge | 1 (7) | 10 | 100 | 0 |

After the extraction was completed by the magnetic bead extractor, the solution to be tested in the columns 6 and 12 of the 96-well plate may be transferred to the 96-well loading plate for detection on the machine. The existing magnetic bead extractor may accommodate two 96-well plates for parallel operation for one time. Therefore, the pretreatment flux is 32 samples/batch; a 96-channel magnetic bead extractor may be also available; and the extraction efficiency is kept same. The pretreatment of the sample 96 may be achieved in 10 min. The pretreatment efficiency is greatly improved to achieve the high degree of automation of clinical sample pretreatment.

Example 5: Effects of Different pH Values of the Buffer Formation Solution on the Extraction Effect of Markers During the incubation, angiotensinogen in the plasma sample will be converted into angiotensin I under the catalysis of renin activity, and due to the addition of the angiotensin converting enzyme, the content of the angiotensin I increases. Therefore, the incubation process will directly affect the content of the angiotensin I in the sample. In this example, the preparation, extraction and detection of the low, moderate and high-quality control samples were performed by the method provided in Example 1. The pH values of the buffer formation solution added to the pre-incubation samples were respectively 4.0, 5.0, 5.5, 6.0 and 7.4; the post-incubation samples were absorbed and extracted by the magnetic bead bonded with a balanced hydrophilic-lipophilic polymer on the surface thereof (HLB magnetic bead, Biosepur, Art.No.: BNMA7300001-0; granularity: 30-50 μm; specific surface area: 600 m$^2$/g and pore diameter: 80 A); after elution, the samples were subjected to liquid chromatography tandem-mass spectrometry to survey the test results of the post-incubation samples at different pH values, thus measuring the peak areas of the angiotensin I in the low, moderate and high quality control samples after incubation, as shown in Table 16.

TABLE 16

Effects of different pH values on the marker (angiotensin I) during the incubation

| Marker/pH | | 4.0 | 5.0 | 5.5 | 6.0 | 7.4 |
|---|---|---|---|---|---|---|
| Angiotensin I in the low quality control sample after incubation | Peak area | 63920 | 98144 | 124610 | 103072 | 96902 |
| | Measured concentration (ng/ml) | 3.21 | 4.67 | 6.03 | 5.25 | 4.47 |
| Angiotensin I in the moderate quality control sample after incubation | Peak area | 122006 | 142264 | 179340 | 157004 | 109414 |
| | Measured concentration (ng/ml) | 5.97 | 7.28 | 8.81 | 7.54 | 5.55 |

TABLE 16-continued

Effects of different pH values on the marker (angiotensin I) during the incubation

| Marker/pH | | 4.0 | 5.0 | 5.5 | 6.0 | 7.4 |
|---|---|---|---|---|---|---|
| Angiotensin I in the high quality control sample after incubation | Peak area | 206258 | 247818 | 291260 | 248104 | 206134 |
| | Measured concentration (ng/ml) | 10.28 | 12.34 | 14.99 | 12.31 | 10.07 |

As can be seen from Table 16, the pH value of the buffer formation solution must be controlled within a suitable scope during the incubation, or, the catalytic activity of renin will be affected seriously, leading to a larger deviation in the angiotensin I generated after the incubation. The measured renin activity is low under nonideal pH conditions, and when ARR is calculated by aldosterone/renin activity, it is easy to cause a higher value of ARR, leading to a false-positive result.

Example 6: Effects of the Different Eluting agent Additives on the Eluting Effects of the Markers In this example, the preparation, extraction and detection of the sample at the minimum concentration point (S1) of the standard curve were performed by the method provided in Example 1. Different additives were added to the eluting agent to prepare different eluting agents, thus eluting the magnetic bead sample; after being eluted, the sample was subjected to liquid chromatography tandem-mass spectrometry to survey the test results of the sample after being eluted by different eluting agents, thus measuring the peak areas of the 5 markers in the sample S1, as shown in Table 17.

As can be seen from Table 17, when methanol is directly used as the eluting agent, each index has poor shape of detection peak and there are serious solvent effects; the situation is improved to some extent when the aqueous solution with 75% methanol is used for elution; and the aqueous solution with 50% methanol may effectively improve the peak shape; the elution efficiency is inadequate when 25% methanol is used; after an acid is added to the eluting agent, the ionization efficiency of aldosterone is obviously inhibited and the peak area decreases, thus affecting the detection sensitivity.

Example 7: Effects of Different Additives on the Test Result of Liquid Chromatography-Tandem Mass Spectrometry In this example, the preparation, extraction and detection of the sample at the minimum concentration point (S1) of the standard curve were performed by the method provided in Example 1. Mobile phase A was an aqueous solution and mobile phase B was a methanol solution (with 5% isopropanol) as basic mobile phases. Different additives were added to the mobile phase A and mobile phase B to prepare different mobile phases for liquid chromatography tandem-mass spectrometry; the test results of the sample detected under different mobile phases were surveyed, thus measuring the peak areas of the 5 markers in the sample S1, as shown in Table 18.

TABLE 17

Effects of different eluting agents on the extraction effects of the markers

| Marker/Eluent solution | | Methanol | Aqueous solution with 75% methanol | Aqueous solution with 50% methanol | Aqueous solution with 25% methanol | Aqueous solution with 0.1% formic acid and aqueous solution with 50% methanol |
|---|---|---|---|---|---|---|
| Angiotensin I (theoretical concentration: 0.3 ng/ml) | Peak area | 4543 | 5784 | 6460 | 5799 | 6620 |
| Angiotensin II (theoretical concentration: 15 pg/ml) | Peak area | 5932 | 6161 | 8967 | 7246 | 6876 |
| Aldosterone (theoretical concentration: 15 pg/ml) | Peak area | 4995 | 3875 | 4563 | 4091 | 2674 |
| Cortisol (theoretical concentration: 1.5 ng/ml) | Peak area | 169965 | 167501 | 163651 | 121041 | 161041 |
| 18-Hydrocorticosterone (theoretical concentration: 12 pg/ml) | Peak area | 707 | 780 | 1019 | 613 | 732 |

TABLE 18

Effects of different additives on the extraction effects of the markers

| Marker/Mobile phase | | Additive-free | 1 mM ammonium fluoride | 0.03% formic acid |
|---|---|---|---|---|
| Angiotensin I (theoretical concentration: 0.3 ng/ml) | Peak area | 4368 | 6460 | 7967 |
| Angiotensin II (theoretical concentration: 15 pg/ml) | Peak area | 8069 | 8967 | 8355 |
| Aldosterone (theoretical concentration: 15 pg/ml) | Peak area | 2668 | 4563 | 1656 |
| Cortisol (theoretical concentration: 1.5 ng/ml) | Peak area | 139964 | 163651 | 147501 |
| 18-Hydrocorticosterone (theoretical concentration: 12 pg/ml) | Peak area | 706 | 1019 | 739 |

As can be seen from Table 18, compared with the condition free of an additive, the addition of 1 mM ammonium fluoride both in the mobile phase A and the mobile phase B may effectively improve the detection sensitivity; but the test result of the sample greatly varies from the type of the additives added; compared with the addition of 0.03% formic acid, the addition of 1 mM ammonium fluoride will cause decreased Ang I response to some extent, but may further improve the detection sensitivity of the other 4 indexes, especially for the low-content aldosterone. Therefore, the detection sensitivity of the 5 markers may satisfy the clinical demand more.

Example 8: Effects of the Selection of Anionic and Cationic Modes on the Detection of Aldosterone In this example, research shows that during the mass spectrometric detection of the 5 markers, the cationic mode should be chosen to detect angiotensin I, angiotensin II, cortisol and 18-hydrocorticosterone, while the anionic mode needs to be chosen to detect aldosterone; this is because when the cationic mode is chosen, there exists a peak diagram of cortisone, an isomer of aldosterone, nearby the detection peak of aldosterone to cause larger interference, and CV % is greater than 15%; but when the anionic mode is applied for detection, the test result is more stable and accurate, and CV% is less than 8.33%.

Example 9: Screening, Confirmed and Typing Diagnosis System for Primary Aldosteronism In this example, a screening, confirmed and typing diagnosis system for primary aldosteronism is used for the screening, confirmed and typing diagnosis of primary aldosteronism; the specific method is as follows:

(1) A marker test module is used to obtain test values of the 5 markers for one time by the method provided by Example 1.

(2) ARR is calculated by a data analysis module and according to the test values of aldosterone and angiotensin I; the calculation formula of the ARR is as follows: ARR=concentration of aldosterone/production rate of angiotensin I; the production rate of angiotensin I is calculated by detecting the concentration of angiotensin I in the pre-incubation sample and in the post-incubation sample and according to the following formula: production rate of angiotensin I=(concentration of angiotensin I after incubation—concentration of angiotensin I before incubation)/incubation time, where the concentration of angiotensin I before incubation is very low and thus, may be basically ignored.

(3) A positive or negative result is judged in combination with a cut-off value 20.4 of the ARR and a concentration of a hypertension therapeutic affecting the ARR (see details in the patent invention 2021106374412 of the prior application). When the test result of ARR is less than 20.4, and if the patient is simultaneously detected to contain the drug capable of reducing ARR in vivo, a false-positive result may be judged, and a confirmed experiment or drug withdrawal needs to be performed for examination. When the test result of ARR is less than 20.4, and if the patient is simultaneously detected to contain the drug capable of increasing ARR in vivo, a positive result may be judged. When the test result of ARR is greater than 20.4, and if the patient is simultaneously detected to contain the drug capable of increasing ARR in vivo, a false-positive result may be judged, and a confirmed experiment or drug withdrawal needs to be performed for examination. When the ARR is greater than 20.4, and if the patient is simultaneously detected to contain the drug capable of reducing ARR in vivo, a positive result may be judged.

(4) When a positive result is judged, the PA typing is performed according to the test values of aldosterone, angiotensin II, cortisol and 18-hydrocorticosterone; the specific typing diagnosis method is as follows:

a, adrenal venous sampling (AVS): SI (a ratio of cortisol in adrenal veins to arterio-venous cortisol) ≥2:1, indicating successful intubation; LI (a ratio of the aldosterone-cortisol ratio at the dominant side to the aldosterone-cortisol ratio at the non-dominant side) ≥2:1, indicating secretion from the dominant side; CI (a ratio of the aldosterone-cortisol ratio at non-dominant side to the arterio-venous aldosterone-cortisol ratio) <1:1, the contralateral is inhibited;

b, 18-hydrocorticosterone (18-OHB): the level of 18-OHB in the plasma of aldosteronoma patients at 8:00 a.m. in a lying position is usually >100 ng/dl, while for the patients with idiopathic aldosteronism, the level of 18-OHB is usually <100 ng/dl;

c, primary and secondary hypertension is subjected to typing diagnosis in combination with the test value of angiotensin II.

Example 10: Selection for the ARR Cut-Off Value 61 cases of patients receiving secondary hypertension screening were chosen in this example, of which 20 cases were diagnosed with PA.

1. Inclusion Criteria

The patients whose standing position PAC was greater than 15 ng/dL, standing position ARR was greater than 30 and aldosterone inhibition ratio after CCT was less than 30% were brought into the group PA. Before screening, the patients were requested to withdraw diuretics or aldosterone receptor antagonists at least for 4 weeks, and other antihypertensive drugs such as, angiotensin converting enzyme inhibitors (ACEI), angiotensin receptor inhibitors (ARB), calcium ion antagonists (CCB) and beta receptor blockers at least for 2 weeks. Before blood sampling, serum potassium should be corrected to the normal range as much as possible. The patients who were grouped into the PA group kept in a standing position at 05:00 a.m. in the following day, and 2 h later, the blood sample was collected in the standing position at 07:00 a.m.

2. AVS Judgment Criteria

Bilateral synchronous blood sampling stimulated by non-adrenocorticotrophic hormone was applied. The content of the 5 markers in the blood sample was detected by the method provided by Example 1. A ratio of cortisol in adrenal veins to arterio-venous cortisol is defined as a selectivity index (SI); SI >2 indicates successful blood sampling. A ratio of the aldosterone-cortisol ratio at the dominant side (a standardized aldosterone value) to the contralateral standardized aldosterone value is defined as a lateralized index (LI); when LI is greater than 2, it is believed that there is unilateral dominant secretion, and when LI is less than 2, it is believed that there is no obvious unilateral dominant secretion.

3. Sample collection: for all the sample collection, the subject was requested to receive the treatment of overnight fasting for 8 h above; sample transfer, centrifugation and separation should be ensured to be completed within 1 h, thus avoiding possible pre-analysis factors. All the samples were kept at −80° C for test before being analyzed.

4. ARR calculation: the content of the 5 markers in the blood sample was detected by the method provided by Example 1. Based on the calculation formula of the ARR: ARR=concentration of aldosterone/renin activity (production rate of angiotensin I); the renin activity is calculated by detecting the concentration of angiotensin I in the pre-incubation sample and in the post-incubation sample and according to the following formula: production rate of angiotensin I=(concentration of angiotensin I after incubation—concentration of angiotensin I before incubation sample)/incubation time, where the concentration of angiotensin I before incubation is very low and thus, may be basically ignored. The screening, confirmed and typing diagnosis system for primary aldosteronism provided in Example 8 was used for the screening, confirmed and typing diagnosis of primary aldosteronism.

5. Analysis by a Statistical Method

The data was processed by R language software. Based on the analysis of the correlation between the ARR value and the presence of PA patients or not, the analysis result is shown in Table 19.

TABLE 19

Comparison of the test result between the ARR value and the presence of PA patients or not

| Criteria | Youden index | Sensitivity | 95% CI | Specificity | 95% CI | +LR | −LR |
|---|---|---|---|---|---|---|---|
| >13.8 | 0.6623 | 94.44 | 72.7-99.9 | 71.79 | 55.1-85.0 | 3.35 | 0.077 |
| >20.4 | 0.8162 | 94.44 | 72.7-99.9 | 87.18 | 72.6-95.7 | 7.37 | 0.064 |
| >29 | 0.7564 | 83.33 | 58.6-96.4 | 92.31 | 79.1-98.4 | 10.83 | 0.18 |
| >37.2 | 0.6709 | 72.22 | 46.5-90.3 | 94.87 | 82.7-99.4 | 14.08 | 0.29 |
| >39.1 | 0.5598 | 61.11 | 35.7-82.7 | 94.87 | 82.7-99.4 | 11.92 | 0.41 |

As can be seen from Table 19, when the ARR cut-off value is 20.4, the detection sensitivity, degree of sensitivity and 95% CI are in higher levels and have obvious advantages relative to other cut-off values. The effect of sensitivity is the most crucial index to judge whether ARR is negative or positive by the screening, confirmed and typing diagnosis system for primary aldosteronism provided by the present invention. Missing detection may be prevented effectively only by high sensitivity. Even though it is false-positive, the false-positive result may be further confirmed by PA typing according to the test values of the subsequent aldosterone, angiotensin II, cortisol and 18-hydrocorticosterone. However, if there is lack of sensitivity, originally positive patients are erroneously judged as negative and thus, are not subjected to the subsequent typing diagnosis, which is very easy to cause missing detection. Therefore, 20.4 is applied as the ARR cut-off value, which may effectively prevent missing detection.

Meanwhile, when LC-MS/MS of the ARR is greater than 20.4, the Youden index is also up to the maximum value (YI=0.82), which indicates that the screening effect of primary aldosteronism is optimal and closest to the real value.

The ARR cut-off value of 20.4 is applied for analysis; and results are shown in Table 20:

TABLE 20

| Analysis result of ARR > 20.4 | |
|---|---|
| ROC area under the curve (AUC) | 0.956 |
| 95% confidence interval b | 0.866-0.993 |
| Significance level P (area = 0.5) | <0.0001 |
| Youden index J | 0.8162 |
| Relative standard | >20.4 |
| Sensitivity | 94.44 |
| Specificity | 87.18 |

Figure 2:
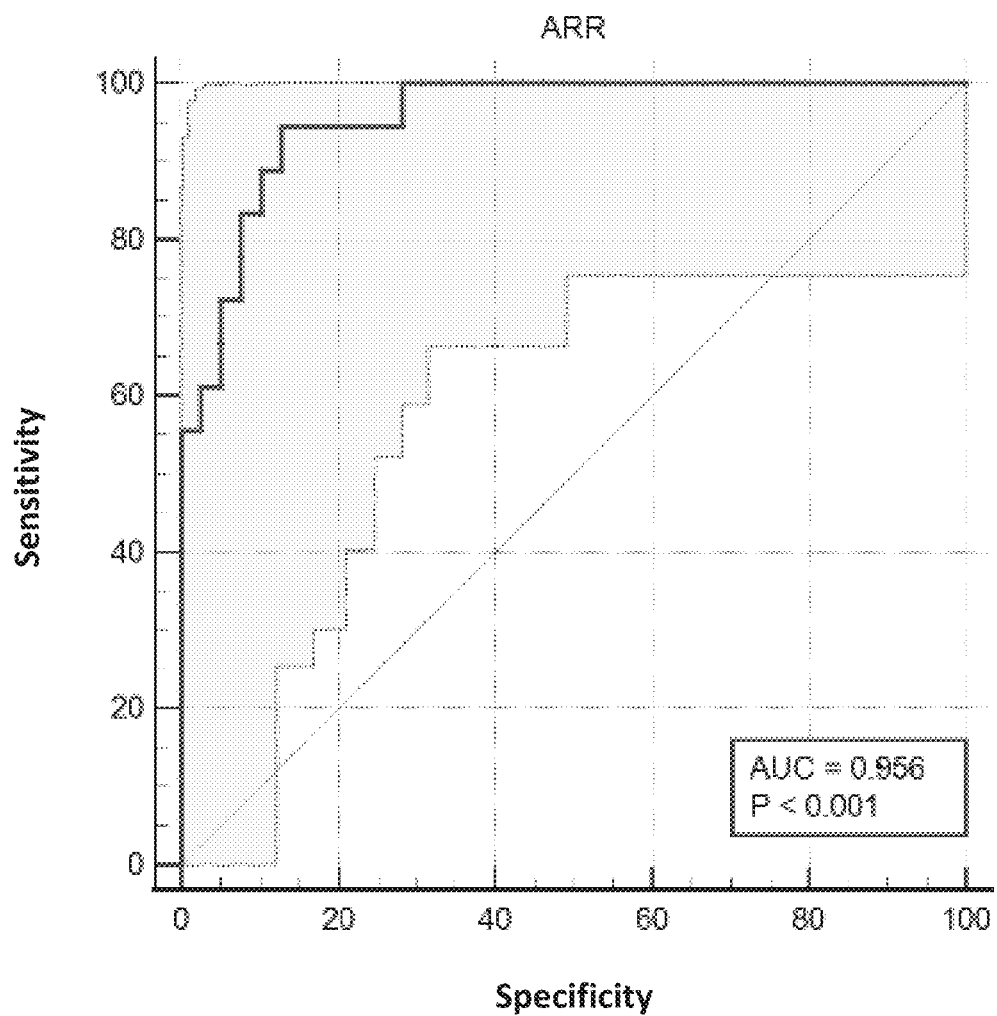
FIG. 2 is a ROC curve graph showing that the ARR cut-off value is 20.4 in Example 10.

As can be seen from Tables 19 and 20, when LC-MS/MS of the ARR is greater than 20.4, the Youden index is also up to the maximum value (YI=0.82); sensitivity and specificity are respectively 94.4% (95% CI:72.7-99.9) and 87.2% (95% CI: 72.6-95.7); area under the curve (AUC) is up to 0.956 (FIG. 2).

The cut-off value of ARR is commonly believed as 30 in the prior art. The cut-off value of ARR needs to be adjusted 20.4 when the screening, confirmed and typing diagnosis system for primary aldosteronism provided in the present invention is applied. This is mainly because the ARR value is directly correlated to the detection sensitivity of aldosterone and renin activity. Aldosterone is universally detected by chemiluminesent immunoassay previously, but the test value is higher such that the calculated result of the ARR value is greater than the actual value. Therefore, it needs to set a cut-off value of 30 to judge whether PA is positive or negative accurately more. When the sample pretreatment (extraction by the magnetic bead bonded with a balanced hydrophilic-lipophilic polymer silica gel) and detection method (HPLC-tandem mass spectrometry) provided by the present invention are applied, the test value may reflect the content of the aldosterone reagent more accurately. Therefore, the previous cut-off value of 30 of ARR has not conformed to the PA screening and typing system provided by the present invention; the cut-off value of ARR needs to be adjusted 20.4 such that the screening and typing result has a higher sensitivity, and the diagnostic result is more accurate.

Even though the present invention is disclosed above, the present invention is not limited thereto. Any person skilled in art can make various alterations and modifications within the spirit and scope of the present invention. Therefore, the protection scope of the present invention shall be subjected to the scope defined by the claims.

The invention claimed is:

1. A screening, confirmed and typing diagnosis system for primary aldosteronism, wherein the system consists of a marker test module, a data input/output interface and a data analysis module; wherein the markers test module is configured to obtain test values of markers by a method of detecting the markers in blood, the data input/output interface is configured to input the test values of five markers, the data analysis module is configured to analyze the test values of the markers, the markers are aldosterone, angiotensin I, angiotensin II, cortisol and 18-hydrocorticosterone; and, wherein after analysis by the data analysis module, the data input/output interface is configured to output a screening, confirmed and typing diagnosis result of primary aldosteronism, wherein the method of detecting the markers in the blood comprises the following steps:
(1) treating a blood sample with a magnetic bead bonded with a balanced hydrophilic-lipophilic polymer on a surface of the magnetic bead to absorb the markers in the blood sample; and
(2) using an eluent solution to eluent the markers from the magnetic bead, and using a liquid chromatography tandem-mass spectrometry to test contents of the markers in the blood sample, wherein the markers are aldosterone, angiotensin I, angiotensin II, cortisol and 18-hydrocorticosterone.

2. The system of claim 1, wherein a method for analyzing the test values of the markers by the data analysis module is as follows: calculating an aldosterone/renin activity ratio (ARR) value based on aldosterone and renin activity and making a judgment in combination with a cut-off value, which is 20.4, of the ARR value and a concentration of a hypertension therapeutic affecting the ARR value; when a positive result is judged, confirmed and typing diagnosis is performed according to the test values of the aldosterone, the angiotensin I, the angiotensin II, the cortisol and the 18-hydrocorticosterone; wherein the rennin activity is a yield of the angiotensin I per unit time.

* * * * *